US008287706B2

(12) United States Patent
Muraoka et al.

(10) Patent No.: US 8,287,706 B2
(45) Date of Patent: Oct. 16, 2012

(54) LAMINATED GAS SENSOR ELEMENT, GAS SENSOR EQUIPPED WITH LAMINATED GAS SENSOR ELEMENT, AND METHOD FOR MANUFACTURING LAMINATED GAS SENSOR ELEMENT

(75) Inventors: Tatsuhiko Muraoka, Aichi (JP); Masaki Mizutani, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 192 days.

(21) Appl. No.: 12/873,120

(22) Filed: Aug. 31, 2010

(65) Prior Publication Data
US 2011/0056832 A1 Mar. 10, 2011

(30) Foreign Application Priority Data
Sep. 4, 2009 (JP) ................................. 2009-204180

(51) Int. Cl.
*G01N 27/407* (2006.01)
(52) U.S. Cl. ......... 204/429; 204/411; 204/424; 204/432
(58) Field of Classification Search .................. 204/410, 204/411, 421, 424–429, 431–433; 205/780.5–787; 73/23.31–23.32
See application file for complete search history.

(56) References Cited

U.S. PATENT DOCUMENTS

| 4,021,326 | A | * | 5/1977 | Pollner et al. ................. 204/429 |
| 5,766,434 | A | * | 6/1998 | Fujii et al. ..................... 204/429 |
| 2002/0008025 | A1 | * | 1/2002 | Fujii et al. ..................... 204/429 |
| 2003/0034245 | A1 | * | 2/2003 | Diehl ............................ 204/424 |
| 2003/0159928 | A1 | * | 8/2003 | Kojima et al. ................ 204/408 |

FOREIGN PATENT DOCUMENTS
JP 2003-322632 A 11/2003
* cited by examiner

*Primary Examiner* — Kaj K Olsen
*Assistant Examiner* — Susan D Leong
(74) *Attorney, Agent, or Firm* — Sughrue Mion, PLLC

(57) ABSTRACT

A laminated gas sensor element including a detection element including a solid electrolyte body having a pair of electrodes formed thereon laminated together with a heater element. A porous protection layer is formed on at least a distal end portion of the laminated gas sensor element which is to be exposed to a gas to be measured. The surface of the porous protection layer has 10 or more small pores each having a diameter of 1 μm to 5 μm inclusive and an aspect ratio of 0.5 to 2.0 inclusive within an area measuring 50 μm×50 μm, and one to less than 20 large pores each having a diameter of 8 μm to 20 μm inclusive and an aspect ratio of 0.5 to 2.0 inclusive within an area measuring 100 μm×100 μm. Also disclosed is a method for manufacturing the laminated gas sensor.

4 Claims, 10 Drawing Sheets

LAMINATED GAS SENSOR ELEMENT, GAS SENSOR EQUIPPED WITH LAMINATED GAS SENSOR ELEMENT, AND METHOD FOR MANUFACTURING LAMINATED GAS SENSOR ELEMENT

BACKGROUND OF THE INVENTION

1. Field of the Invention

The present invention relates to a laminated gas sensor element, a gas sensor equipped with the laminated gas sensor element, and a method for manufacturing the laminated gas sensor element.

2. Description of the Related Art

Conventionally, known gas sensors include those for detecting a particular gas component contained in exhaust gas or for measuring the concentration of the particular gas component. Some of these gas sensors employ a laminated gas sensor element configured such that a pair of electrodes are provided on a solid electrolyte body. The solid electrolyte body of zirconia or the like used in the gas sensor element becomes active at a high temperature of 300° C. or higher. Usually, the gas sensor element is used in an activated state upon heating by a heater laminated on the solid electrolyte body. In this case, adhesion, to the gas sensor element, of a water or oil droplet contained in a gas to be measured (hereinafter, also referred to as adhesion of water) may generate a crack in the gas sensor element due to thermal shock. According to a known technique for solving this problem, a distal end portion (detecting portion) of the gas sensor element which is exposed to a gas to be measured is protected with a porous protection layer. For example, Patent Document 1 discloses a technique for restraining the generation of a crack at corner portions of a gas sensor element by increasing the thickness of a protection layer at the corner portions, which are susceptible to the generation of a crack.

[Patent Document 1] Japanese Patent Application Laid-Open (kokai) No. 2003-322632

3. Problems to be Solved by the Invention

However, even in the case of a laminated gas sensor element whose detecting portion is protected with a porous protection layer as in the case of Patent Document 1, the protection layer may fail to provide sufficient protection. Namely, adhesion thereto of a larger amount of water droplets or oil droplets contained in a gas to be measured (adhesion of water), potentially results in the generation of a crack in the laminated gas sensor element due to thermal shock.

SUMMARY OF THE INVENTION

It is therefore an object of the present invention to provide a technique for more reliably restraining the generation of a crack in a gas sensor element which could otherwise result from adhesion of water.

In a first aspect (1), the present invention provides a laminated gas sensor element for detecting a particular gas component contained in a gas to be measured, which comprises a detection element comprising a solid electrolyte body having thereon a pair of electrodes; and a heater element containing a heat-generating resistor, wherein the detection element is laminated together with the heater element. A porous protection layer is formed on at least a distal end portion of the laminated gas sensor element which is to be exposed to the gas to be measured. A surface of the porous protection layer has 10 or more small pores each having a diameter of 1 µm to 5 µm inclusive and an aspect ratio of 0.5 to 2.0 inclusive within an area measuring 50 µm×50 µm, and one to less than 20 large pores each having a diameter of 8 µm to 20 µm inclusive and an aspect ratio of 0.5 to 2.0 inclusive within an area measuring 100 µm×100 µm.

In the laminated gas sensor element (1), the surface (i.e., exposed surface) of the porous protection layer has small pores and large pores having appropriate sizes and formed in appropriate numbers. Thus, even upon adhesion of water to the gas sensor element, the generation of a crack in the gas sensor element can be restrained.

Specifically, in the case where the number of large pores within an area measuring 100 µm×100 µm is less than one, the large pores fail to absorb thermal shrinkage of the porous protection layer. As a result, a crack or fissure is apt to generate in the porous protection layer. In the case where the number of large pores within an area measuring 100 µm×100 µm is 20 or more, the strength of the porous protection layer deteriorates, or water droplets and the like are apt to reach the gas sensor element through the large pores, resulting in deterioration in resistance to water adhesion.

In the case where the number of small pores within an area measuring 50 µm×50 µm is less than 10, only a limited effect of improving evaporation of water droplets and the like can be provided as compared with the case where only large pores are formed. Therefore, only a limited effect of improving resistance to water adhesion can be realized.

In a preferred embodiment (2) of the laminated gas sensor element according to (1) above, the porous protection layer has a porosity of 15% to 65% inclusive as measured on the surface thereof.

In the laminated gas sensor element (2), since the porous protection layer has a porosity of 15% to 65% inclusive as measured on the outer surface thereof, the generation of a crack can be sufficiently restrained. Notably, "porosity" is the percentage of the area of pores in a unit area of the surface of the porous protection layer. The porosity can be determined, for example, from an enlarged photograph obtained with a scanning electron microscope. In a porous protection layer having a porosity less than 15%, a gas to be measured encounters difficulty in passing therethrough. Consequently, accuracy in gas detection may deteriorate. In a porous protection layer having a porosity in excess of 65%, the degree of penetration of water droplets and the like is high. As a result, the effect of restraining the generation of a crack which could otherwise result from adhesion of water may not be sufficiently realized.

In a preferred embodiment (3) of the laminated gas sensor element according to (1) or (2) above, the porous protection layer has a thickness of 50 µm to 500 µm inclusive.

In the laminated gas sensor element (3), since the porous protection layer has a thickness of 50 µm to 500 µm inclusive, the generation of a crack can be restrained more effectively. When the thickness of the porous protection layer is less than 50 µM, the porous protection layer may be too thin to allow water droplets and the like to slowly penetrate while dispersing therethrough. When the thickness of the porous protection layer is in excess of 500 µm, the volume of the gas sensor element increases. Consequently, the time required for activation of the gas sensor element increases, potentially resulting in deterioration in measuring accuracy of the gas sensor. Notably, the thickness of the porous protection layer indicates an average thickness.

In a second aspect (4), the present invention provides a gas sensor comprising a laminated gas sensor element according to any of (1) to (3) above.

In the gas sensor (4), a distal end portion of the laminated gas sensor element is covered with the porous protection layer having small pores and large pores having appropriate sizes and formed in appropriate numbers. Thus, even upon adhesion of water to the gas sensor element, the generation of a crack in the gas sensor element can be restrained.

In a third aspect (5), the present invention provides a method for manufacturing a laminated gas sensor element adapted to detect a gas component contained in a gas to be measured, the laminated gas sensor element comprising a detection element comprising a solid electrolyte body having thereon a pair of electrodes; and a heater element containing a heat-generating resistor, wherein the detection element is laminated together with the heater element, and a porous protection layer is formed on at least a distal end portion of the laminated gas sensor element which is to be exposed to the gas to be measured, which method comprises a step of forming the porous protection layer, said step of forming the porous protection layer comprises (a) mixing two or more volatile solvents of differing vapor pressure into a material powder for forming the porous protection layer so as to obtain a coating liquid; (b) applying the coating liquid to a distal end portion of the laminated gas sensor element so as to cover the distal end portion; and (c) firing the laminated gas sensor element to which the coating liquid has been applied, so as to form the porous protection layer on the distal end portion of the laminated gas sensor element.

In the method (5) for manufacturing a laminated gas sensor element, since two or more volatile solvents having different respective vapor pressures are mixed for obtaining a coating liquid, the surface of the porous protection layer can have small pores and large pores having appropriate sizes and formed in appropriate numbers. Therefore, the method (5) for manufacturing a laminated gas sensor element makes possible the manufacture of a laminated gas sensor element which is unlikely to crack even upon adhesion of water thereto.

In a preferred embodiment (6) for manufacturing a laminated gas sensor element according to (5) above, a difference in vapor pressure between the at least two of the volatile solvents used in step (a) is 0.5 kPa or greater.

In the method (6) for manufacturing a laminated gas sensor, since the difference in vapor pressure between the volatile solvents is 0.5 kPa or greater, the surface of the porous protection layer can have small pores and large pores having appropriate sizes and formed in appropriate numbers. Therefore, the method (6) for manufacturing a laminated gas sensor element makes possible the manufacture of a laminated gas sensor element which is unlikely to crack even upon adhesion of water thereto.

In a preferred embodiment (7) for manufacturing a laminated gas sensor element according to (6) above, the two or more volatile solvents used in step (a) include an ether-based solvent and a gasoline-based solvent.

Since the two or more volatile solvents used in the method (7) for manufacturing a laminated gas sensor element include an ether-based solvent and a gasoline-based solvent, the surface of the porous protection layer can have small pores and large pores having appropriate sizes and formed in appropriate numbers. Therefore, the method (7) for manufacturing a laminated gas sensor element makes possible the manufacture of a laminated gas sensor element which is unlikely to crack even upon adhesion of water thereto.

The present invention can be embodied in various forms; for example, as a method, apparatus, or system for manufacturing a gas sensor.

DESCRIPTION OF REFERENCE NUMERALS

Figure 1:
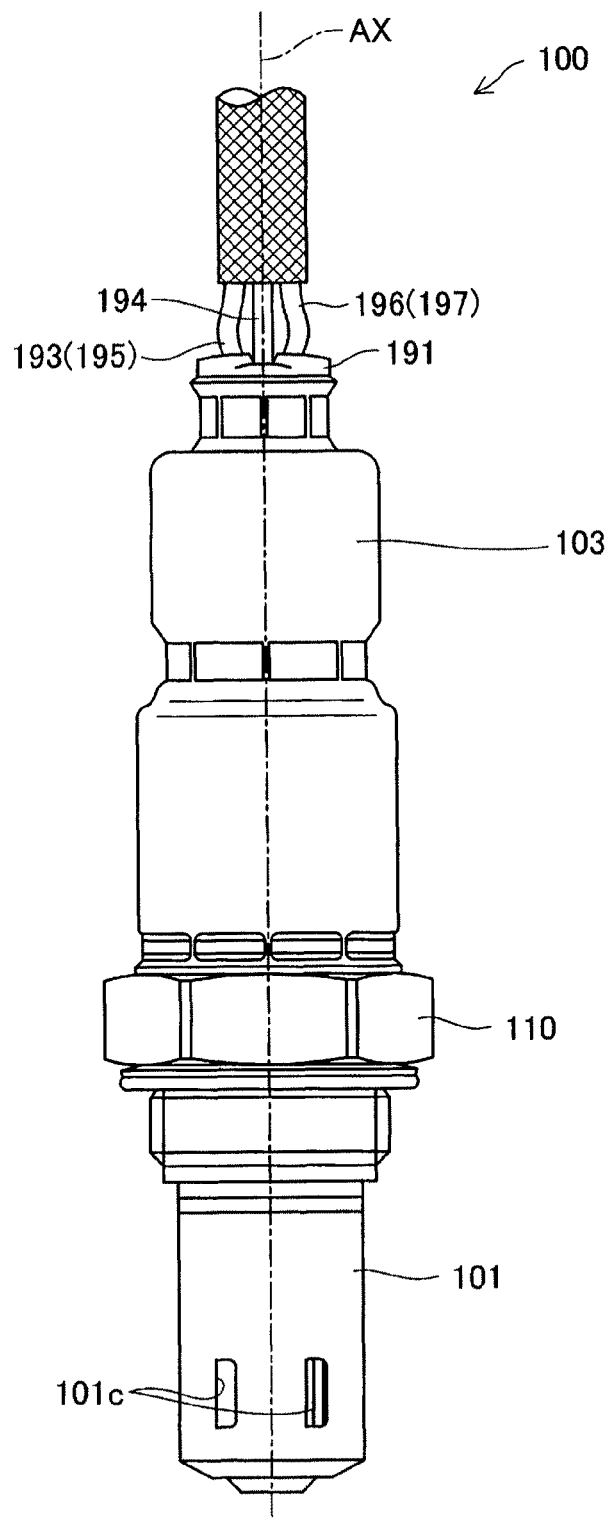
FIG. 1 is an external view showing a gas sensor 100 according to an embodiment of the present invention.

Reference numerals used to identify various structural features in the drawings include the following.
100: gas sensor
101: protector
101c: introduction hole
103: metal sleeve
110: metallic shell
110k: proximal end portion
111: ledge portion
113: ceramic holder
114: first powder layer
115: second powder layer
116: metal cup
117: crimp ring
120: laminated gas sensor element
120a: first plate surface
120b: second plate surface
121: gas detection section
124: porous protection layer
125: sensor electrode pad (Ip electrode pad)
126: sensor electrode pad (COM electrode pad)
127: sensor electrode pad (Vs electrode pad)
128: heater electrode pad
129: heater electrode pad
130: detection element
131: protection layer
131a: first surface
132: porous body
133: through hole conductor
134: through hole conductor
135: through hole conductor
136: pump cell
137: first solid electrolyte layer
137a: first surface
137b: second surface
138: first electrode portion
139: first lead portion
140: second electrode portion
141: second lead portion
142: through hole conductor 143: through hole conductor
145: spacer
145c: gas detection chamber
146: diffusion control layer
147: through hole conductor
148: through hole conductor
149: electromotive cell
150: second solid electrolyte layer
150a: first surface
150b: second surface
151: third electrode portion
152: third lead portion
153: fourth electrode portion
154: fourth lead portion
155: through hole conductor
160: heater element
161: first insulation layer
162: second insulation layer
162b: second surface
163: heat-generating resistor
164: heater lead portion
165: heater lead portion
166: through hole conductor
167: through hole conductor
170: ceramic sleeve
170c: axial hole
181: separator
181c: opening
182: sensor connection terminal
183: sensor connection terminal
184: sensor connection terminal
185: heater connection terminal
186: heater connection terminal
190: urging metal member
191: grommet
193: sensor lead wire
194: sensor lead wire
195: sensor lead wire
196: heater lead wire
197: heater lead wire

DETAILED DESCRIPTION OF THE PREFERRED EMBODIMENTS

Figure 2:
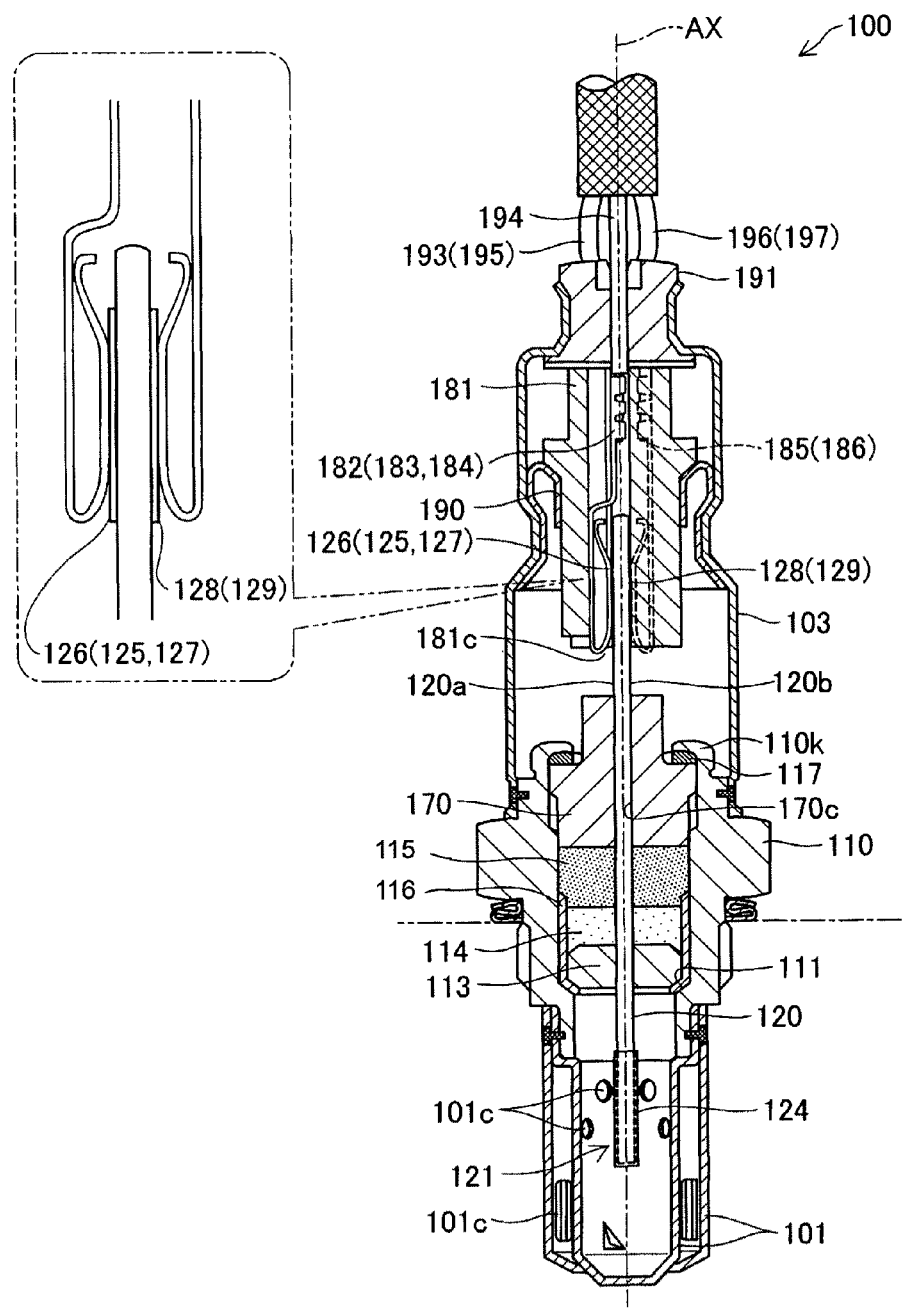
FIG. 2 is a sectional view showing the gas sensor 100.

An embodiment of the present invention will next be described in the following sequence and with reference to the drawings. However, the present invention should not be construed as being limited thereto.
A. Configuration of gas sensor
B. Configuration of gas sensor element
C. Porous protection layer on distal end portion of gas sensor element
D. Method for manufacturing porous protection layer
E. Water adhesion resistance test
F. Modifications A. Configuration of Gas Sensor:

FIG. 1 is an external view of a gas sensor 100 according to an embodiment of the present invention. FIG. 2 is a sectional view of the gas sensor 100. In FIGS. 1 and 2, the lower side corresponds to a distal side with respect to a direction of axis AX, and the upper side corresponds to a proximal side with respect to the direction of axis AX. The gas sensor 100 is a full range air/fuel ratio sensor attached to an exhaust pipe of an internal combustion engine, and is adapted to linearly detect the concentration of oxygen contained in exhaust gas. On the basis of an oxygen concentration detected by the gas sensor 100, an electronic control unit (not shown) mounted in a vehicle performs feedback control on the air/fuel ratio of an air-fuel mixture to be supplied to the internal combustion engine.

As shown in FIGS. 1 and 2, the gas sensor 100 includes a tubular metallic shell 110 extending in the direction of axis AX; a gas sensor element 120 disposed inside the metallic shell 110; a tubular ceramic sleeve 170, through which the gas sensor element 120 is inserted and thereby supported by the tubular ceramic sleeve 170; and a separator 181 attached to a proximal end portion of the gas sensor element 120.

As shown in FIG. 2, the interior of the metallic shell 110 has a ledge portion 111 projecting radially inward. Within the metallic shell 110, a tubular ceramic holder 113 made of alumina, a first powder layer 114 made of talc powder, a second powder layer 115 made of talc powder, and the tubular ceramic sleeve 170 made of alumina are disposed in this order from the distal side toward the proximal side. Also, a tubular metal cup 116 is disposed within the metallic shell 110. Further, the tubular metal cup 116 is united with the gas sensor element 120, along with the ceramic holder 113 and the first powder layer 114. Yet further, a crimp ring 117 is disposed between the ceramic sleeve 170 and a proximal end portion 110k of the metallic shell 110.

The ceramic holder 113 is disposed within the metal cup 116 and engaged at its distal end portion with the ledge portion 111 of the metallic shell 110 via the metal cup 116. The gas sensor element 120 is inserted through the ceramic holder 113. The entire first powder layer 114 is disposed within the metal cup 116. Further, the second powder layer 115 ensures gastightness between the metallic shell 110 and the gas sensor element 120.

The ceramic sleeve 170 is a tubular body which has an axial hole 170c having a rectangular cross section and extending along the axis AX. The ceramic sleeve 170 supports the gas sensor element 120 such that the plate-like gas sensor element 120 is inserted through the rectangular axial hole 170c along the axis AX. After the ceramic sleeve 170 is fitted into the metallic shell 110, the proximal end portion 110k of the metallic shell 110 is bent radially inward for crimping toward the proximal end surface of the ceramic sleeve 170 via the crimp ring 117, to thereby fix the ceramic sleeve 170 in the metallic shell 110.

A distal end portion of the gas sensor element 120 projects from the metallic shell 110. Thus, a double-structured, closed-bottomed tubular protector 101 is laser-welded to a distal end portion of the metallic shell 110 so as to cover the distal end portion of the gas sensor element 120 projecting from the metallic shell 110. The protector 101 has a plurality of introduction holes 101c formed at predetermined positions for introducing exhaust gas therethrough into the gas sensor 100 attached to an exhaust pipe.

A gas detection section 121 configured to detect the oxygen concentration of exhaust gas is provided at a distal end portion of the gas sensor element 120 fixed to the ceramic sleeve 170 disposed in the metallic shell 110. Further, a porous protection layer 124 is formed at the distal end portion of the gas sensor element 120 so as to cover the gas detection section 121. The porous protection layer 124 can restrain adhesion of water droplets and oil droplets contained in exhaust gas to the gas detection section 121 heated to a high temperature by a heater and can restrain the generation of a crack in the gas sensor element 120. The gas sensor element 120 and the porous protection layer 124 is described in detail below.

A proximal end portion of the gas sensor element 120 projects from the metallic shell 110 toward the separator 181. The proximal end portion of the gas sensor element 120 has three sensor electrode pads (an electromotive-cell electrode pad (Vs electrode pad) 125, a COM electrode pad 126, and a pump-cell electrode pad (Ip electrode pad) 127) provided on a first plate surface 120a and electrically communicating with the gas detection section 121, and two heater electrode pads 128 and 129 provided on a second plate surface 120b and electrically communicating with a heat-generating resistor 163, described below.

The electrode pads of the gas sensor element 120 are connected to respective terminals inserted into the separator 181. This is described below. As shown in FIG. 2, a tubular metal sleeve 103 is laser-welded to a proximal end portion of the metallic shell 110. The separator 181 is disposed within the metal sleeve 103. Three sensor connection terminals 182, 183 and 184 and two heater connection terminals 185 and 186 are disposed within the separator 181. The separator 181 accommodates the sensor connection terminals 182, 183 and 184 and the heater connection terminals 185 and 186 so as to isolate and prevent the connection terminals from contacting one another.

A proximal end portion of the gas sensor element 120 projecting from a proximal end portion of the ceramic sleeve 170 is inserted into the separator 181 through an opening 181c of the separator 181. The sensor connection terminals 182, 183 and 184 are in elastic contact with the sensor electrode pads 125, 126 and 127 of the gas sensor element 120, respectively, to thereby establish electrical connection therebetween. The heater connection terminals 185 and 186 are in elastic contact with the heater electrode pads 128 and 129 of the gas sensor element 120, respectively, to thereby establish electrical connection therebetween. The enlarged view appearing at the left side of FIG. 2 facilitates understanding of a state of contact between the connection terminals and the electrode pads provided on the gas sensor element 120. The separator 181 is held within the metal sleeve 103 while being urged against a grommet 191, described below, by means of a substantially tubular urging metal member 190 disposed around the separator 181.

The grommet 191 made of a fluorine-containing rubber is disposed in a proximal end portion of the metal sleeve 103. Three sensor lead wires 193, 194 and 195 and two heater lead wires 196 and 197 are inserted through the grommet 191. Distal end portions of the sensor lead wires 193, 194 and 195 are inserted into the separator 181 and crimped to the sensor connection terminals 182, 183 and 184, to thereby establish electrical connection therebetween. Distal end portions of the heater lead wires 196 and 197 are inserted into the separator 181 and crimped to the heater connection terminals 185 and 186, to thereby establish electrical connection therebetween. The sensor lead wire 193 is connected to the Ip electrode pad 125 of the gas sensor element 120 via the sensor connection terminal 182. The sensor lead wire 194 is connected to the COM electrode pad 126 of the gas sensor element 120 via the sensor connection terminal 183. The sensor lead wire 195 is connected to the Vs electrode pad 127 of the gas sensor element 120 via the sensor connection terminal 184.

Figure 3:
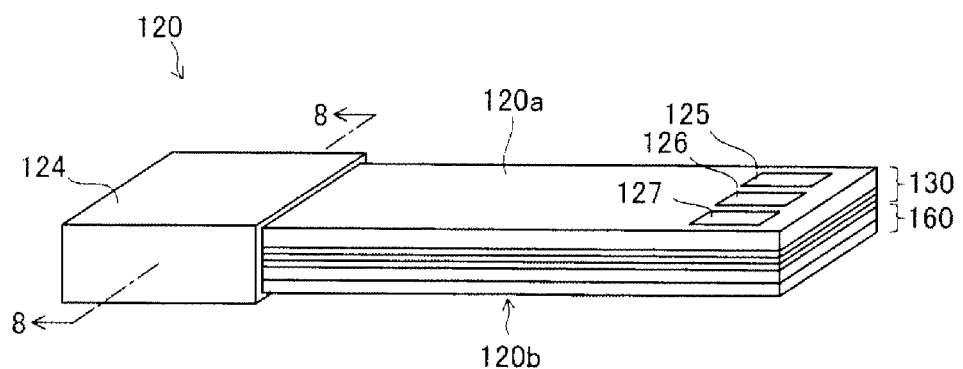
FIG. 3 is an explanatory view showing a gas sensor element 120 on which a porous protection layer 124 is formed.
Figure 4:
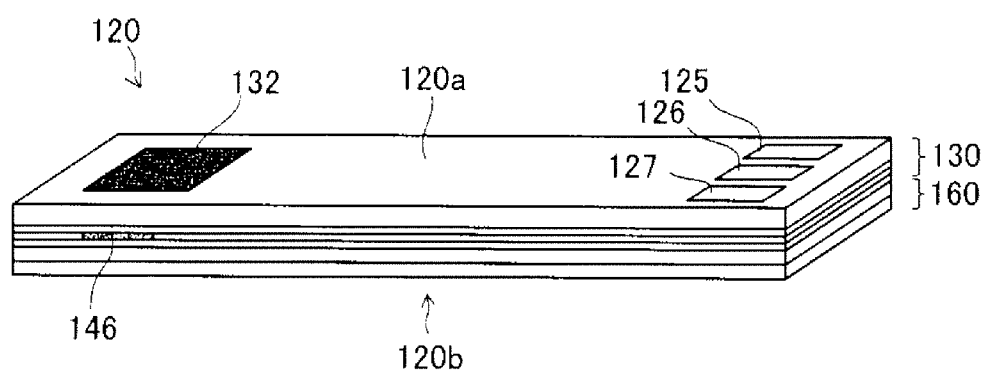
FIG. 4 is an explanatory view showing the gas sensor element 120 as viewed before formation of the porous protection layer 124.

B. Configuration of Gas Sensor Element:

FIG. 3 is an explanatory view showing the gas sensor element 120 on which the porous protection layer 124 is formed. FIG. 4 is an explanatory view showing the gas sensor element 120 as viewed before formation of the porous protection layer 124. The gas sensor element 120 is formed as follows: a plate-like detection element 130 extending in an axial direction (in a horizontal direction in FIGS. 3 and 4) and a plate-like heater element 160 extending in the axial direction are laminated together, followed by firing to integrate the same. In FIGS. 3 and 4, the left side corresponds to the distal side in FIGS. 1 and 2, and the right side corresponds to the proximal side in FIGS. 1 and 2. This also applies to FIG. 5 described below.

Figure 5:
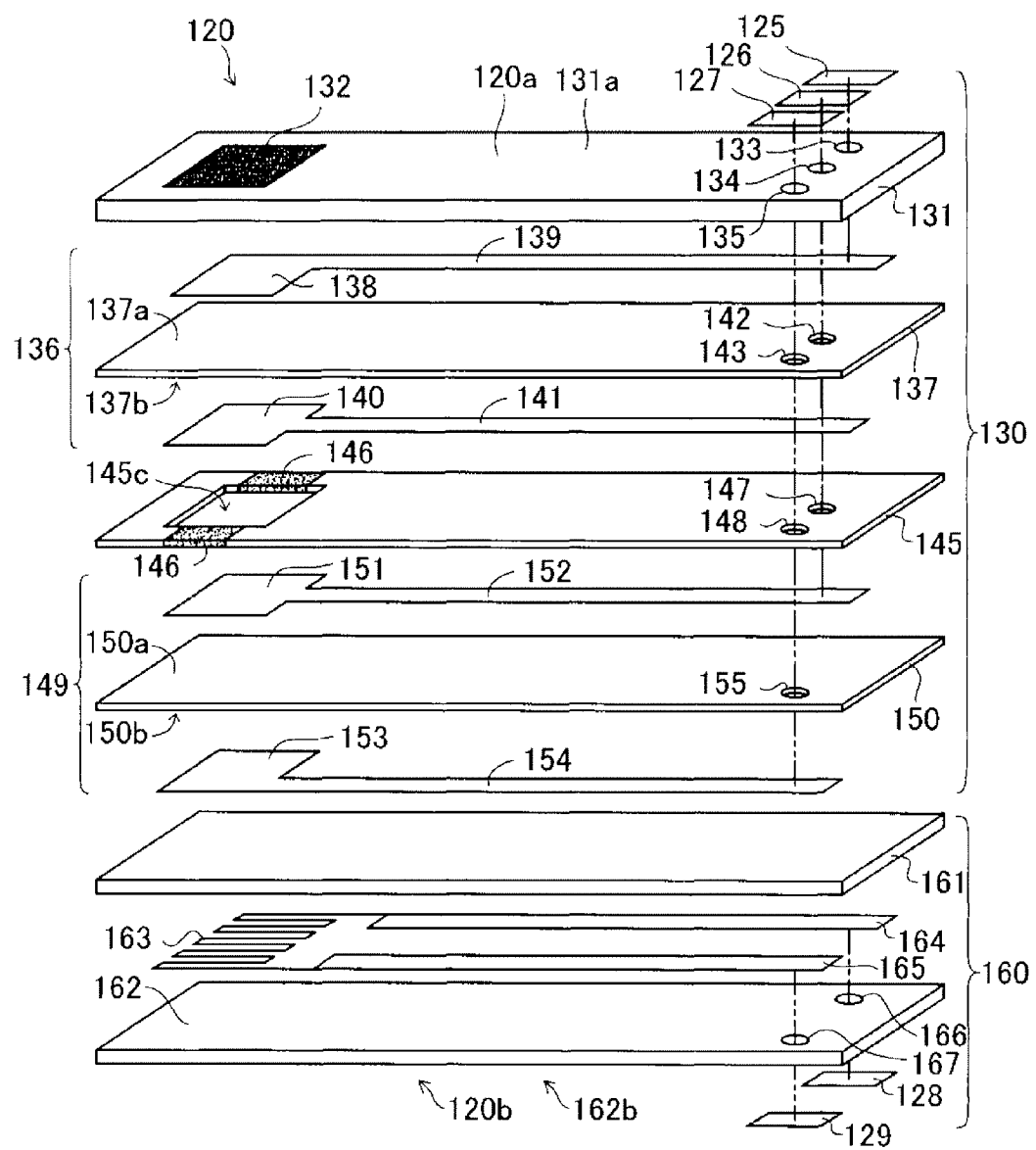
FIG. 5 is an exploded explanatory view showing the gas sensor element 120.

FIG. 5 is an exploded explanatory view showing the gas sensor element 120. The detection element 130 is configured such that a plate-like protection layer 131, a plate-like first solid electrolyte layer 137, a plate-like spacer 145, and a plate-like second solid electrolyte layer 150 are laminated together in this order from a side corresponding to the first plate surface 120a toward a side corresponding to the second plate surface 120b.

The protection layer 131 is formed mainly of alumina. A distal end portion of the protection layer 131 has a porous body 132 formed therein. The aforementioned three sensor electrode pads; i.e., the Ip electrode pad 125, the COM electrode pad 126 and the Vs electrode pad 127, are formed on a first surface 131a of the protection layer 131, which serves as the first plate surface 120a of the gas sensor element 120, in the vicinity of the proximal end of the first surface 131a at predetermined intervals along a direction perpendicular to the axial direction. The protection layer 131 has three through hole conductors 133, 134 and 135 formed therethrough in the vicinity of the proximal end thereof. The Ip electrode pad 125, the COM electrode pad 126 and the Vs electrode pad 127 are electrically connected to the through hole conductors 133, 134 and 135, respectively, as indicated by the broken lines in FIG. 5.

The first solid electrolyte layer 137 is formed mainly of zirconia and has two through hole conductors 142 and 143 formed therethrough in the vicinity of the proximal end thereof. The through hole conductors 142 and 143 are electrically connected to the through hole conductors 134 and 135, respectively, formed through the protection layer 131.

A first surface 137a (upper surface in FIG. 5) of the first solid electrolyte layer 137 has a rectangular, porous first electrode portion 138 formed thereon and formed mainly of Pt. The first electrode portion 138 is electrically connected, via a first lead portion 139, to the through hole conductor 133 formed through the protection layer 131. Accordingly, the first electrode portion 138 electrically communicates with the Ip electrode pad 125 through the through hole conductor 133. The first electrode portion 138 is exposed to exhaust gas through the porous body 132 provided in the protection layer 131.

A second surface 137b (lower surface in FIG. 5) of the first solid electrolyte layer 137 has a rectangular, porous second electrode portion 140 formed thereon and formed mainly of Pt. The second electrode portion 140 is electrically connected, via a second lead portion 141, to the through hole conductor 142 formed through the first solid electrolyte layer 137. Accordingly, the second electrode portion 140 electrically communicates with the COM electrode pad 126 through the through hole conductor 142 and the through hole conductor 134. The first solid electrolyte layer 137 and the paired first and second electrode portions 138 and 140 constitute a pump cell 136.

The spacer 145 is formed mainly of alumina and has a rectangular opening formed at a distal end portion thereof. When the spacer 145 is sandwiched between the first solid electrolyte layer 137 and the second solid electrolyte layer 150, the rectangular opening forms a gas detection chamber 145c. A diffusion control layer 146 is formed in a portion of each of opposite side walls of the gas detection chamber 145c for controlling diffusion of gas into the gas detection chamber 145c from the ambient atmosphere. The diffusion control layers 146 are formed of porous alumina. The spacer 145 has two through hole conductors 147 and 148 formed therethrough in the vicinity of a proximal end portion thereof. The through hole conductor 147 is electrically connected to the through hole conductor 142 formed through the first solid electrolyte layer 137. The through hole conductor 148 is electrically connected to the through hole conductor 143 formed through the first solid electrolyte layer 137.

The second solid electrolyte layer 150 is formed mainly of zirconia and has a through hole conductor 155 formed therethrough in the vicinity of a proximal end portion thereof The through hole conductor 155 is electrically connected to the through hole conductor 148 formed through the spacer 145.

A first surface 150a (upper surface in FIG. 5) of the second solid electrolyte layer 150 has a rectangular, porous third electrode portion 151 formed thereon and formed mainly of Pt. The third electrode portion 151 is electrically connected, via a third lead portion 152, to the through hole conductor 147 formed through the spacer 145. Accordingly, the third electrode portion 151 electrically communicates with the COM electrode pad 126 through the through hole conductor 147, the through hole conductor 142 and the through hole conductor 134. That is, the third electrode portion 151 and the second electrode portion 140 are connected in common to the COM electrode pad 126 and have the same electric potential.

A second surface 150b (lower surface in FIG. 5) of the second solid electrolyte layer 150 has a rectangular, porous fourth electrode portion 153 formed thereon and formed mainly of Pt. The fourth electrode portion 153 is electrically connected, via a fourth lead portion 154, to the through hole conductor 155 formed through the second solid electrolyte layer 150. Accordingly, the fourth electrode portion 153 electrically communicates with the Vs electrode pad 127 through the through hole conductor 155, the through hole conductor 148, the through hole conductor 143 and the through hole conductor 135. The second solid electrolyte layer 150 and the paired third and fourth electrode portions 151 and 153 constitute an electromotive cell 149.

The heater element 160 is configured such that a plate-like first insulation layer 161 and a plate-like second insulation layer 162 are laminated together in this order from a side corresponding to the first plate surface 120a toward a side corresponding to the second plate surface 120b. The first insulation layer 161 and the second insulation layer 162 are formed of alumina. The heat-generating resistor 163 having a meandering shape and formed mainly of Pt is disposed between the first insulation layer 161 and the second insulation layer 162 at a distally located position. Heater lead portions 164 and 165 extend from respective opposite ends of the heat-generating resistor 163 toward the proximal end of the heater element 160.

The second insulation layer 162 has two through hole conductors 166 and 167 formed therethrough in the vicinity of the proximal end thereof. The aforementioned two heater electrode pads 128 and 129 are formed on a second surface 162b of the second insulation layer 162, which serves as the second plate surface 120b of the gas sensor element 120, in the vicinity of the proximal end of the second surface 162b at a predetermined interval along a direction perpendicular to the axial direction. The heater electrode pad 128 is electrically connected to the heater lead portion 164 via the through hole conductor 166. The heater electrode pad 129 is electrically connected to the heater lead portion 165 via the through hole conductor 167.

The thus-configured gas sensor 100 is attached to the exhaust pipe of an internal combustion engine and operates in the following manner. First, a heater control circuit (not shown) causes the heater element 160 to heat the gas sensor 100 to several hundred ° C. (e.g., 700° C. to 800° C.), thereby activating the pump cell 136 and the electromotive cell 149. Further, a very small current Icp (about 15 µA) is applied to the electromotive cell 149 through the Vs electrode pad 127, thereby causing the fourth electrode portion 153 to function as an oxygen reference chamber. In this condition, when the atmosphere within the gas detection chamber 145c is held at a stoichiometric air-fuel ratio, a predetermined voltage (e.g., 450 mV) is generated between the electromotive cell 149 and the oxygen reference chamber, whose oxygen concentration is held at a substantially constant level. Thus, by use of a predetermined electric circuit having a known configuration, control is performed so as to hold the atmosphere within the gas detection chamber 145c at a stoichiometric air-fuel ratio by means of adjusting the current Ip applied to the pump cell 136 such that voltage Vs of the electromotive cell 149 becomes 450 mV. Through such operation of the gas sensor 100, on the basis of the current Ip required for holding the interior of the gas detection chamber 145c at the stoichiometric air-fuel ratio, the concentration of oxygen contained in exhaust gas can be measured.

Figure 6:
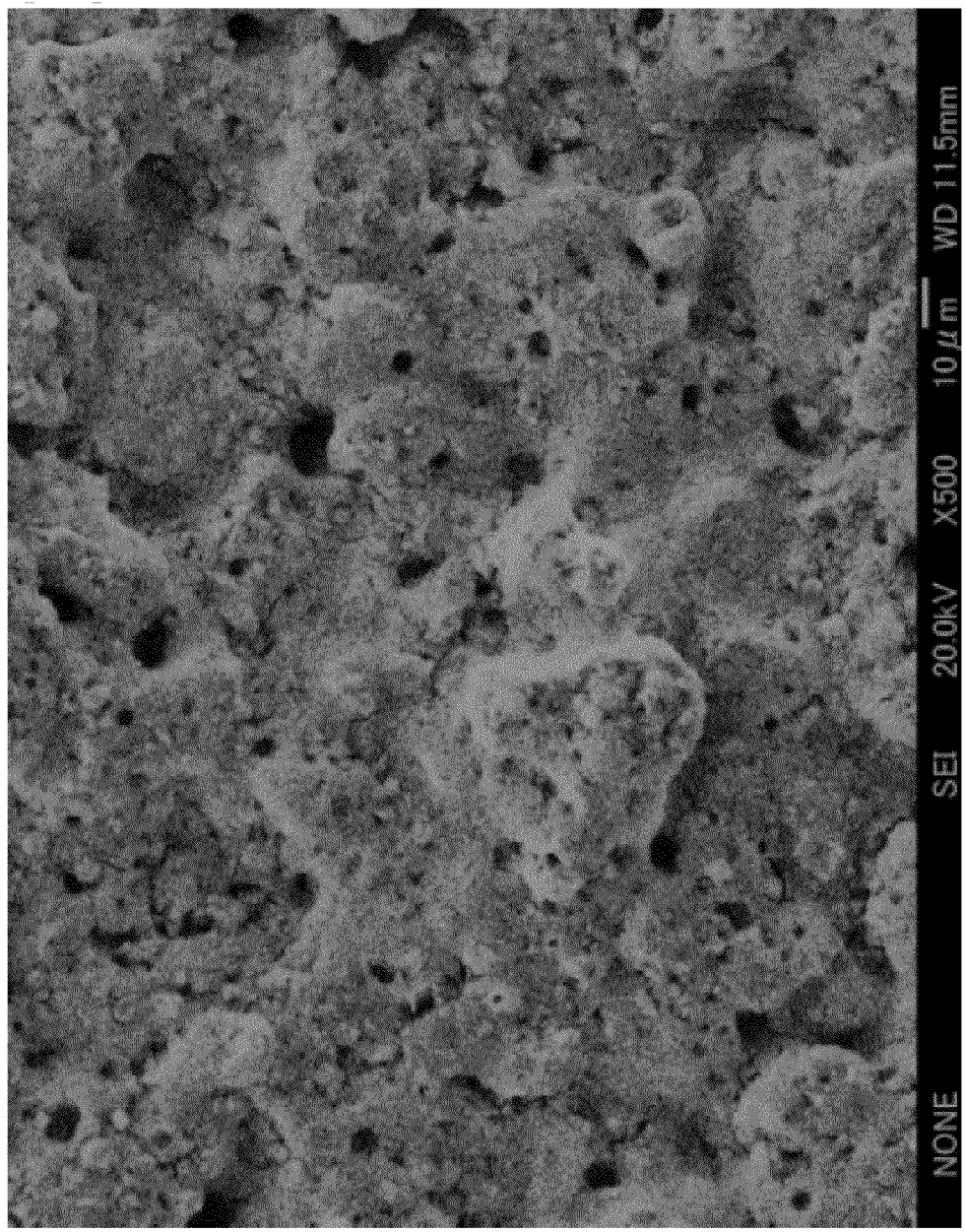
FIG. 6 is an explanatory view showing the surface of the porous protection layer 124 as observed through a scanning electron microscope.

C. Porous Protection Layer on Distal End Portion of Gas Sensor Element:

FIG. 6 is an explanatory view showing the surface of the porous protection layer 124 as observed through a scanning electron microscope. The surface of the porous protection layer 124 has small pores each having a diameter of 1 µm to 5 µm inclusive and an aspect ratio of 0.5 to 2.0 inclusive and large pores each having a diameter of 8 µm to 20 µm inclusive, and an aspect ratio of 0.5 to 2.0 inclusive.

Figure 7:
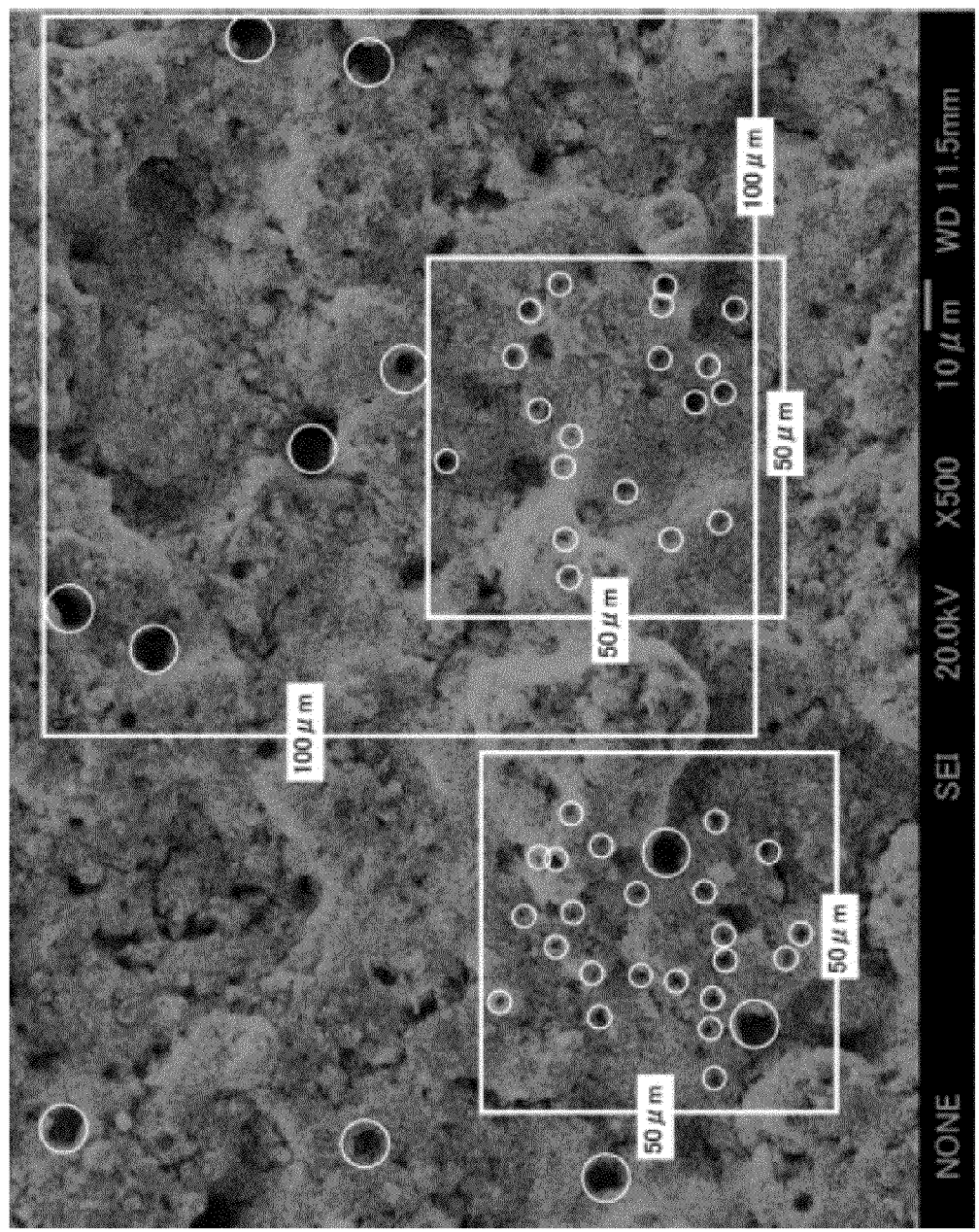
FIG. 7 is an explanatory view showing small pores and large pores on the surface of the porous protection layer 124 of FIG. 6 in which the pores are marked with circles.

FIG. 7 is an explanatory view showing the small pores and the large pores on the surface of the porous protection layer 124 of FIG. 6 in such a manner that the pores are marked with respective circles. Exhaust gas to be measured by the gas sensor 100 can reach the diffusion control layers 146 of the gas sensor element 120 through the small pores and the large pores. Meanwhile, since water droplets and the like generated from exhaust gas to be measured adhere to the porous protection layer 124, direct contact of water droplets and the like with the surface of the gas sensor element 120 is restrained. Specifically, when water droplets and the like adhere to the porous protection layer 124, the water droplets and the like are divided into individual droplets having such a size so as to pass through the small pores and the large pores. In the course of passing through the porous protection layer 124, most of such droplets evaporate before reaching the surface of the gas sensor element 120. Particularly, when water droplets and the like pass through the small pores, the water droplets and the like are smaller in volume as compared with those which pass through the large pores, and thus are more likely to evaporate. Therefore, by forming the porous protection layer 124 shown in FIGS. 6 and 7, the generation of a crack in the gas sensor element 120 can be restrained which could otherwise result from adhesion of water droplets and the like.

Next, the number of small pores and that of large pores will be explained. In FIG. 7, two square frames each measuring 50 µm×50 µm appear, and 10 or more small pores are present within each of the frames (in the present embodiment, 23 small pores and 19 small pores, respectively). Further, in FIG. 7, a square frame measuring 100 µm×100 µm appears, and one to less than 20 large pores are present within the frame (in the present embodiment, six large pores). The square frames appearing in FIG. 7 are mere examples. On the surface of the porous protection layer 124, an arbitrary area measuring 50

μm×50 μm contains 10 or more small pores, and an arbitrary area measuring 100 μm×100 μm contains one to less than 20 large pores.

In the case where the number of large pores present within the frame measuring 100 μm×100 μm is less than one, the large pores fail to absorb thermal shrinking stress of the porous protection layer 124. As a result, a crack or fissure is apt to be generated in the porous protection layer 124. In the case where the number of large pores within the frame measuring 100 μm×100 μm is 20 or more, the strength of the porous protection layer 124 deteriorates, or water droplets and the like are apt to reach the gas sensor element 120 through the large pores, resulting in deterioration in resistance to water adhesion. Therefore, preferably, the number of large pores within an area measuring 100 μm×100 μm on the surface of the porous protection layer 124 is one to less than 20.

In the case where the number of small pores within the frame measuring 50 μm×50 μm is less than 10, only a limited effect can be obtained of improving evaporation of water droplets and the like as compared with the case where only large pores are formed. Therefore, only a limited effect of improving resistance to water adhesion can be attained. Accordingly, preferably, the number of small pores within an area measuring 50 μm×50 μm on the surface of the porous protection layer 124 is 10 or more. In the case where the number of small pores within the frame measuring 50 μm×50 μm is 50 or more, the strength of the porous protection layer 124 may decrease. Therefore, preferably, the number of small pores within an area measuring 50 μm×50 μm on the surface of the porous protection layer 124 is less than 50.

Next, the porosity of the porous protection layer 124 as measured on the surface thereof will be described. The porosity of the porous protection layer 124 as measured on the surface thereof is 15% to 65% inclusive (in the present embodiment, 45%). Notably, "porosity" is the percentage of the area of pores in a unit area of the surface of the porous protection layer 124. Porosity can be obtained from an enlarged photograph obtained using a scanning electron microscope. In the porous protection layer 124 having a porosity less than 15%, exhaust gas encounters difficulty in passing therethrough; consequently, accuracy in gas detection may deteriorate. In the porous protection layer 124 having a porosity in excess of 65%, the degree of penetration of water droplets and the like is high. As a result, the effect of restraining the generation of a crack which could otherwise result from adhesion of water may not be sufficiently realized. Therefore, preferably, the porous protection layer 124 has a porosity of 15% to 65% inclusive as measured on the surface thereof.

Figure 8:
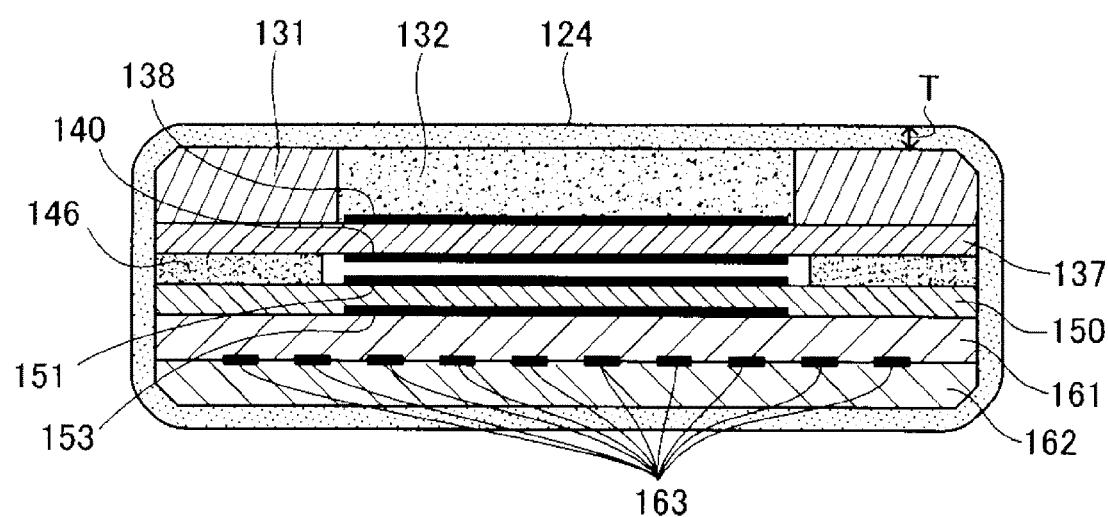
FIG. 8 is an explanatory sectional view taken along line 8-8 of FIG. 3.

FIG. 8 is an explanatory sectional view taken along line 8-8 of FIG. 3. Preferably, in order to effectively restrain the generation of a crack in the gas sensor element 120 which could otherwise result from adhesion of water droplets and oil droplets contained in exhaust gas, the porous protection layer 124 has a thickness T of 50 μm or more. When the thickness T of the porous protection layer 124 is less than 50 μm, the porous protection layer 124 may be too thin to allow water droplets and the like to slowly penetrate while dispersing therethrough. Therefore, preferably, the thickness T of the porous protection layer 124 is 50 μm or more. When the thickness T of the porous protection layer is in excess of 500 μm, the volume of the gas sensor element 120 increases. Consequently, the time required for activating the gas sensor element 120 increases, potentially deteriorating the measuring accuracy of the gas sensor. Therefore, in view of time required for activating the gas sensor element 120, the upper limit of the thickness T of the porous protection layer 124 is preferably 500 μm or less, more preferably 300 μm or less. In the present embodiment, the thickness of the porous protection layer 124 is on average 400 μm.

Figure 9:
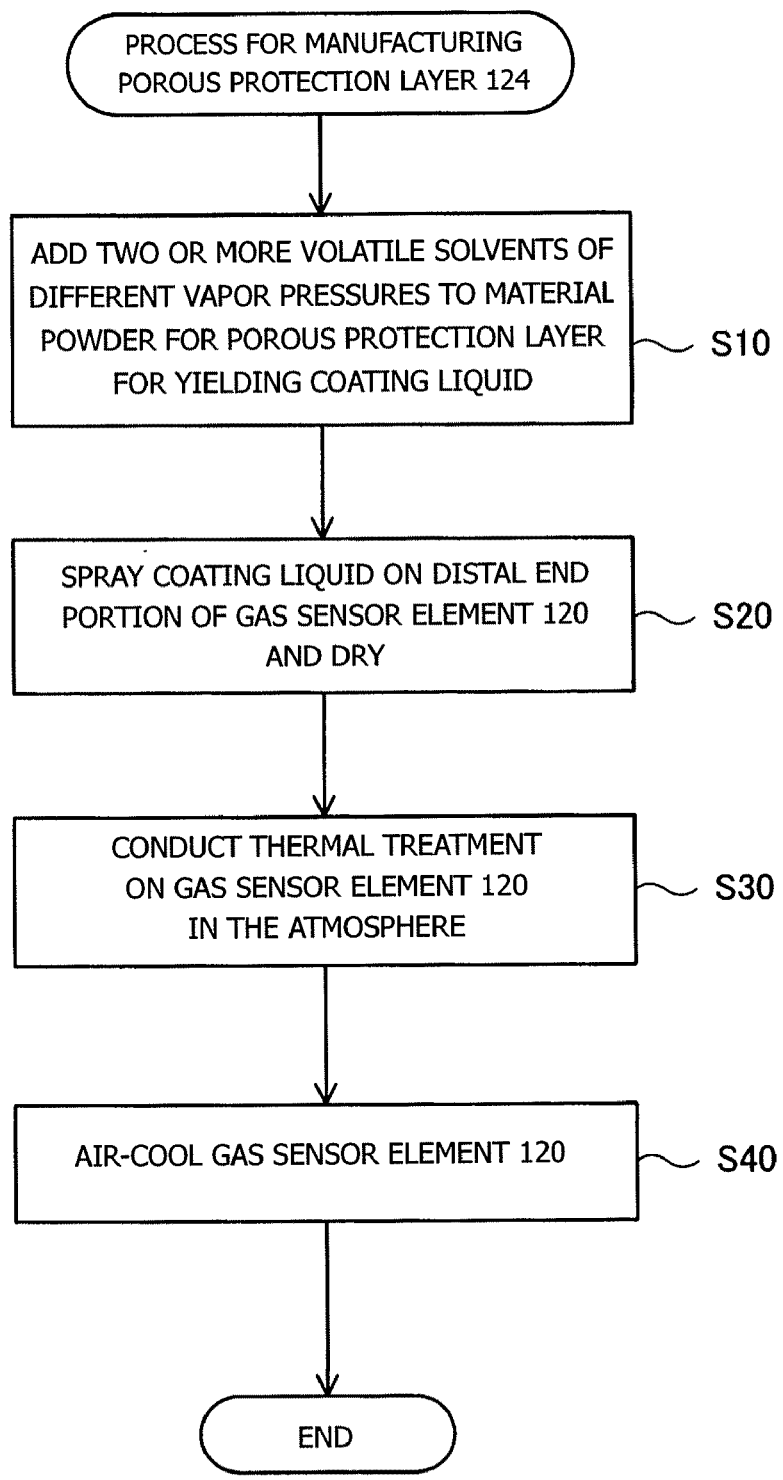
FIG. 9 is a flowchart showing a process for manufacturing the porous protection layer 124.

D. Method for Manufacturing Porous Protection Layer:

FIG. 9 is a flowchart showing a process for manufacturing the porous protection layer 124. In step S10, spinel powder and titania powder are mixed for use as a material for the porous protection layer 124. To the resultant mixture, two or more volatile solvents of differing vapor pressure are added, to thereby obtain a coating liquid. The present embodiment uses a mixed liquid of an ether-based solvent (vapor pressure: 1.20 kPa) and a gasoline-based solvent (vapor pressure: 0.42 kPa), which are volatile solvents. In step S20, the coating liquid thus prepared is sprayed on a distal end portion of the gas sensor element 120, followed by drying. In this manner, a green porous protection layer 124 is formed.

The thickness T of the porous protection layer 124 can be adjusted by adjusting the spraying amount of the coating liquid. Specifically, for example, the spraying amount is adjusted by shifting the spraying zone or inserting a shield plate between a spray and the gas sensor element 120. Also, the thickness T of the porous protection layer 124 can be adjusted by changing the viscosity of the volatile solvents, the spraying time period, the spraying distance, etc.

In step S30, the gas sensor element 120 on which the green porous protection layer 124 is formed is subjected to the following thermal treatment: the temperature of gas sensor element 120 is increased by applying heat in an inert gas atmosphere and the gas sensor element is held at a maximum temperature of 1,000° C. for one hour. After the thermal treatment, the gas sensor element 120 is air-cooled (step S40), whereby the porous protection layer 124 having small pores and large pores as shown in FIGS. 6 and 7 can be formed.

E. Water Adhesion Resistance Test:

In order to study the relationship between resistance to water adhesion and the surface condition (the number of large pores and small pores) of the porous protection layer 124, a water adhesion resistance test was conducted using three kinds of laminated gas sensor element samples which differ in surface condition of the porous protection layer 124. The three kinds of samples are described below, and the procedure for the water adhesion resistance test will be described later.

Samples #1 to #10 are gas sensor elements 120 each having the porous protection layer 124 having the surface shown in FIGS. 6 and 7. Specifically, the surfaces of the porous protection layers 124 of Samples #1 to #10 have one to less than 20 large pores within an area measuring 100 μm×100 μm and 10 to less than 50 small pores within an area measuring 50 μm×50 μm. Notably, the porous protection layers 124 of Samples #1 to #10 differ only in thickness T and have the same surface condition.

Figure 10:
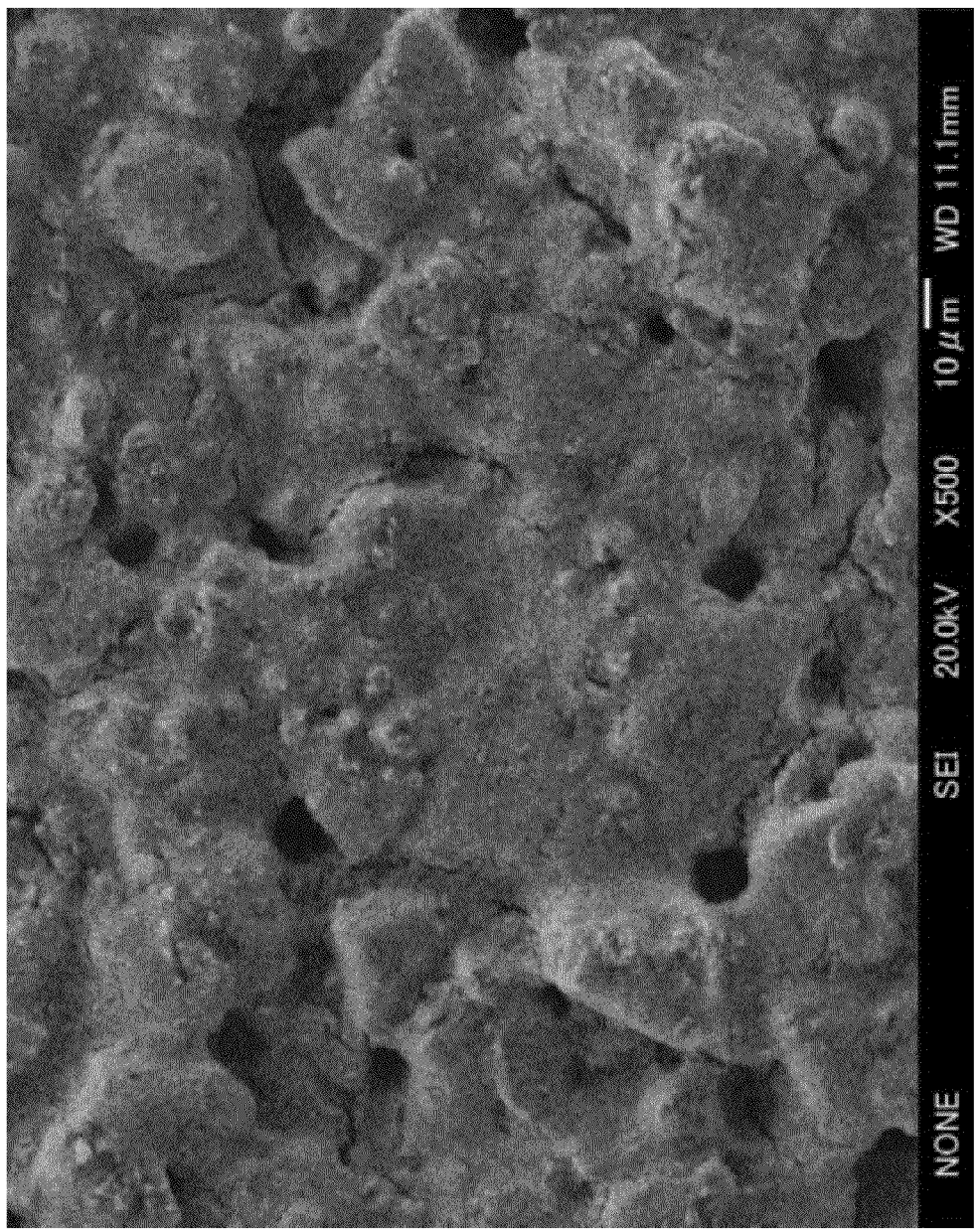
FIG. 10 is an explanatory view showing the surface of the porous protection layer 124 of Samples #11 to #20 as observed through a scanning electron microscope.
Figure 11:
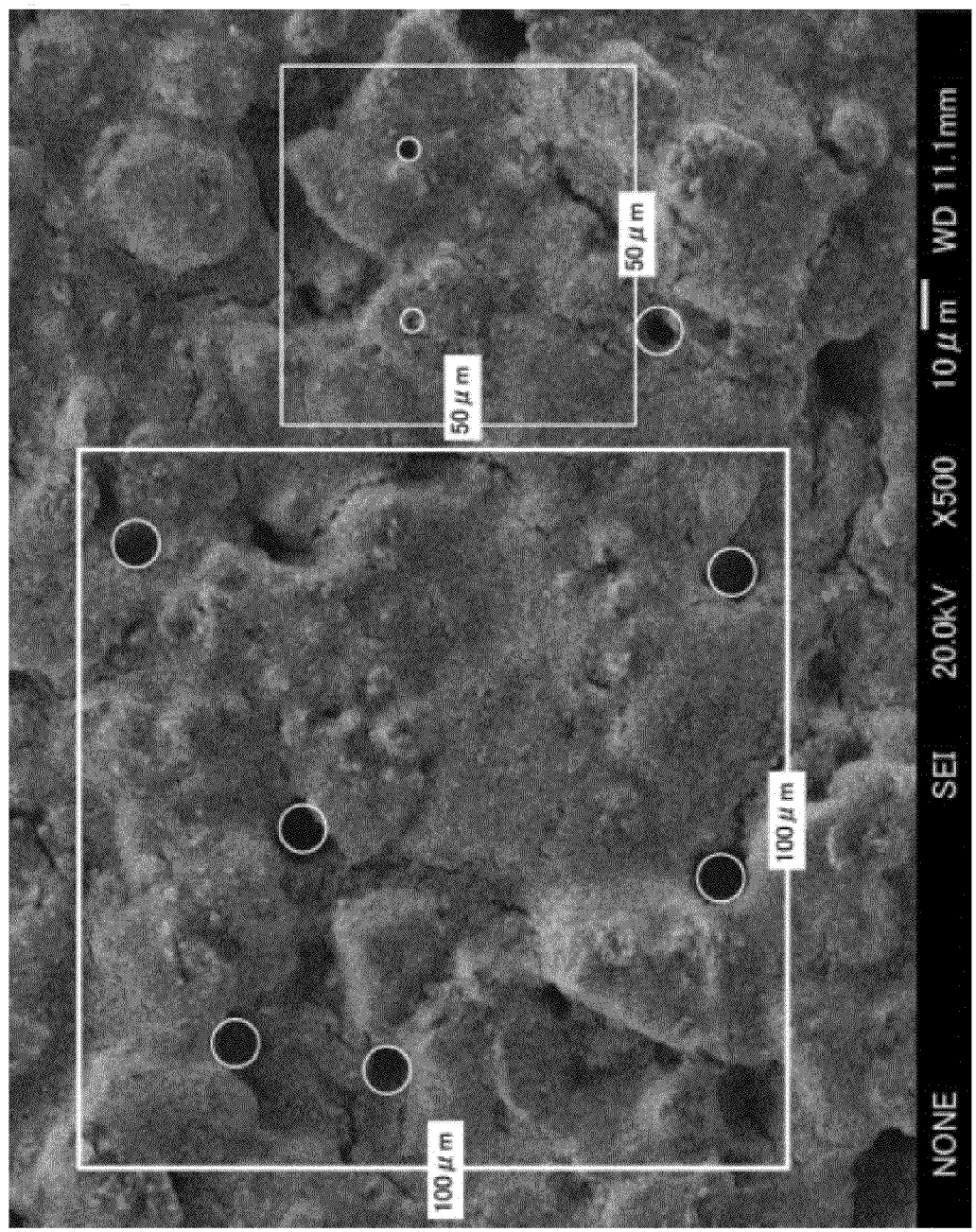
FIG. 11 is an explanatory view showing small pores and large pores on the surface of the porous protection layer 124 of FIG. 10 in which the pores are marked with circles.

FIG. 10 is an explanatory view showing the surface of the porous protection layer 124 of Samples #11 to #20 as observed through a scanning electron microscope. FIG. 11 is an explanatory view showing small pores and large pores on the surface of the porous protection layer 124 of FIG. 10 in which the respective pores are marked with circles. The porous protection layers 124 of Samples #11 to #20 differ merely in thickness T and have the same surface condition. The surfaces of the porous protection layers 124 of Samples #11 to #20 have a predetermined number of large pores each having a diameter of 8 μm to 20 μm inclusive and an aspect ratio of 0.5 to 2.0 inclusive, but hardly have small pores each having a diameter of 1 μm to 5 μm inclusive and an aspect ratio of 0.5 to 2.0 inclusive. Specifically, the surfaces of the porous protection layers 124 of Samples #11 to #20 have one to less than 20 large pores within an area measuring 100 μm×100 μm and less than 10 small pores within an area measuring 50 μm×50 μm.

The method for manufacturing the porous protection layers 124 of Samples #11 to #20 differs from that of the porous protection layers 124 of Samples #1 to #10 in that, instead of adding two or more volatile solvents differing in vapor pressure to a mixed powder of spinel powder and titania powder for obtaining a coating liquid, only ether serving as a sole volatile solvent is added to the mixture. Other manufacturing steps are similar to those for Samples #1 to #10.

Further, the surfaces of the porous protection layers 124 of Samples #21 to #23 have a predetermined number of small pores each having a diameter of 1 μm to 5 μm inclusive and an aspect ratio of 0.5 to 2.0 inclusive, but have large pores each having a diameter of 8 μm to 20 μm inclusive and an aspect ratio of 0.5 to 2.0 inclusive in a predetermined number or more. Specifically, the surfaces of the porous protection layers 124 of Samples #21 to #23 have 20 or more large pores within an area measuring 100 μm×100 μm and less than 10 small pores within an area measuring 50 μm×50 μm. The porous protection layers 124 of Samples #21 to #23 differ merely in thickness T and have the same surface condition.

The method for manufacturing the porous protection layers 124 of Samples #21 to #23 is similar to that for manufacturing the porous protection layers 124 of Samples #11 to #20 except for a mixing ratio of spinel powder and titania powder. That is, the method for manufacturing the porous protection layers 124 of Samples #21 to #23 uses ether alone as a volatile solvent for obtaining a coating liquid.

The water adhesion resistance test was conducted on the above-mentioned three kinds of Samples #1 to #23 by the following procedure.

(1) A thermocouple is attached to the gas detection section 121 of the laminated gas sensor element 120 of each Sample, and the heater is activated so as to heat the gas detection section 121 to a temperature of 800° C. to 900° C.

(2) The initial voltage of the pump cell 136 is measured.

(3) By using a microsyringe, a predetermined amount of water is dripped on the porous protection layer 124 twenty consecutive times.

(4) The voltage of the pump cell 136 is again measured. When the measured voltage deviates from the initial voltage by 1% or greater, the porous protection layer 124 is judged to suffer the generation of a crack.

(5) When a deviation of 1% or greater from the initial voltage is not observed, the amount of water for each dripping is increased, and the above-mentioned steps (3) and (4) are repeated until a deviation of 1% or greater from the initial voltage is observed.

Table 1 below shows the results of the water adhesion resistance test. In the table, "Good" indicates that a deviation of 1% or greater from the initial voltage did not occur; i.e., the porous protection layer 124 was judged to be free from the generation of a crack. In contrast, "Poor" indicates the occurrence of a deviation of 1% or greater from the initial voltage; i.e., the porous protection layer 124 was judged to suffer the generation of a crack in the porous protection layer 124. The symbol "-" indicates that the water adhesion resistance test was not conducted due to the generation of a crack in the porous protection layer 124.

In the case where the amount of dripped water was 0.25 μL, all of Samples #1 to #10 (the number of large pores: one to less than 20; the number of small pores: 10 to less than 50) were evaluated as "Good"; only three Samples of Samples #11 to #20 (the number of large pores: one to less than 20; the number of small pores: less than 10) were evaluated as "Good"; and none of Samples #21 to #23 (the number of large pores: 20 or more; the number of small pores: less than 10) was evaluated as "Good." In the case where the amount of dripped water was 0.30 μL, five Samples of Samples #1 to #10 were evaluated as "Good"; and only one Sample of Samples #11 to #20 was evaluated as "Good." In the case where the amount of dripped water was 0.35 μL, two Samples of Samples #1 to #10 were evaluated as "Good"; and all of Samples #11 to #20 were evaluated as "Poor." Sample #5 (the number of large pores: six; the number of small pores: 30) was evaluated as "Good" up to an amount of dripped water of 0.45 μL.

TABLE 1

| Sample | | Surface condition | | Thickness of protection layer μm | Amount of dripped water μL | | | | | | | | | |
|---|---|---|---|---|---|---|---|---|---|---|---|---|---|---|
| | | Number of large pores 100 μm sq. | Number of small pores 50 μm sq. | | 0.05 | 0.10 | 0.15 | 0.20 | 0.25 | 0.30 | 0.35 | 0.40 | 0.45 | 0.50 |
| #1 | Number of | 5 | 23 | 291 | Good | Good | Good | Good | Good | Poor | — | — | — | — |
| #2 | large pores: | 7 | 26 | 292 | Good | Good | Good | Good | Good | Poor | — | — | — | — |
| #3 | one to less | 6 | 28 | 294 | Good | Good | Good | Good | Good | Poor | — | — | — | — |
| #4 | than 20 | 5 | 25 | 295 | Good | Good | Good | Good | Good | Poor | — | — | — | — |
| #5 | Number of | 6 | 30 | 304 | Good | Good | Good | Good | Good | Good | Good | Good | Good | Poor |
| #6 | small pores: | 5 | 26 | 306 | Good | Good | Good | Good | Good | Good | Good | Poor | — | — |
| #7 | 10 to less | 5 | 24 | 308 | Good | Good | Good | Good | Good | Good | Poor | — | — | — |
| #8 | than 50 | 5 | 22 | 312 | Good | Good | Good | Good | Good | Good | Poor | — | — | — |
| #9 | | 8 | 20 | 323 | Good | Good | Good | Good | Good | Poor | — | — | — | — |
| #10 | | 7 | 25 | 330 | Good | Good | Good | Good | Good | Good | Poor | — | — | — |
| #11 | Number of | 7 | 2 | 297 | Good | Good | Good | Good | Poor | — | — | — | — | — |
| #12 | large pores: | 5 | 1 | 298 | Good | Good | Good | Poor | — | — | — | — | — | — |
| #13 | one to less | 8 | 3 | 298 | Good | Good | Poor | — | — | — | — | — | — | — |
| #14 | than 20 | 5 | 4 | 308 | Good | Good | Good | Poor | — | — | — | — | — | — |
| #15 | Number of | 7 | 2 | 314 | Good | Good | Poor | — | — | — | — | — | — | — |
| #16 | small pores: | 5 | 3 | 315 | Good | Good | Good | Good | Good | Poor | — | — | — | — |
| #17 | less than 10 | 6 | 2 | 319 | Good | Good | Good | Poor | — | — | — | — | — | — |
| #18 | | 6 | 1 | 319 | Good | Good | Good | Good | Poor | — | — | — | — | — |
| #19 | | 5 | 2 | 332 | Good | Good | Good | Good | Good | Good | Poor | — | — | — |
| #20 | | 6 | 3 | 334 | Good | Good | Good | Good | Good | Poor | — | — | — | — |
| #21 | Number of | 23 | 2 | 301 | Good | Good | Poor | — | — | — | — | — | — | — |

TABLE 1-continued

| | | Surface condition | | | Amount of dripped water μL | | | | | | | | | |
|---|---|---|---|---|---|---|---|---|---|---|---|---|---|---|
| Sample | | Number of large pores 100 μm sq. | Number of small pores 50 μm sq. | Thickness of protection layer μm | 0.05 | 0.10 | 0.15 | 0.20 | 0.25 | 0.30 | 0.35 | 0.40 | 0.45 | 0.50 |
| #22 | large pores: 20 or more Number of small pores: less than 10 | 25 | 2 | 313 | Good | Good | Good | Poor | — | — | — | — | — | — |
| #23 | | 26 | 1 | 298 | Good | Good | Good | Poor | — | — | — | — | — | — |

The above-noted test results show that Samples #1 to #10 (the number of large pores: one to less than 20; the number of small pores: 10 to less than 50) are superior in water adhesion resistance to Samples #11 to #20 (the number of large pores: one to less than 20; the number of small pores: less than 10) and Samples #21 to #23 (the number of large pores: 20 or more; the number of small pores: less than 10). Therefore, on the surface of the porous protection layer 124, a number of large pores of one to less than 20 within an area measuring 100 μm×100 μm is preferred, and a number of small pores of 10 to less than 50 within an area measuring 50 μm×50 μm is preferred.

F. Modifications:

The present invention is not limited to the above-described embodiment, but may be embodied in various forms without departing from the gist of the invention. Possible non-limiting modifications include the following.

F1. Modification 1:

In the above-described embodiment, a coating liquid is applied to the gas sensor element 120 by use of a spray. However, the gas sensor element 120 may be immersed in the coating liquid for applying the coating liquid to the gas sensor element 120.

F2. Modification 2:

In the above-described embodiment, a mixture of spinel powder and titania powder is used as material for the porous protection layer 124. However, a ceramic powder which contains predominantly an alumina powder, a mullite powder, or the like can be used as the material.

F3. Modification 3:

In the above-described embodiment, an ether-based solvent (vapor pressure: 1.20 kPa) and a gasoline-based solvent (vapor pressure: 0.42 kPa) are used as two or more volatile solvents of differing vapor pressure. However, two or more volatile solvents having a vapor pressure difference of 0.5 kPa or greater may be used.

It should further be apparent to those skilled in the art that various changes in form and detail of the invention as shown and described above may be made. It is intended that such changes be included within the spirit and scope of the claims appended hereto.

This application claims priority from Japanese Patent Application No. JP 2009-204180 filed Sep. 4, 2009, incorporated herein by reference in its entirety.

What is claimed is:

1. A laminated gas sensor element for detecting a gas component contained in a gas to be measured, comprising:
    a detection element comprising a solid electrolyte body having thereon a pair of electrodes; and
    a heater element containing a heat-generating resistor,
    wherein the detection element is laminated together with the heater element,
    a porous protection layer is formed on at least a distal end portion of the laminated gas sensor element which is to be exposed to the gas to be measured; and
    an outer surface of the porous protection layer has 10 or more small pores each having a diameter of 1 μm to 5 μm inclusive and an aspect ratio of 0.5 to 2.0 inclusive within an area measuring 50 μm×50 μm, and one to less than 20 large pores each having a diameter of 8 μm to 20 μm inclusive and an aspect ratio of 0.5 to 2.0 inclusive within an area measuring 100 μm×100 μm.

2. The laminated gas sensor element as claimed in claim 1, wherein the porous protection layer has a porosity of 15% to 65% inclusive as measured on the outer surface thereof.

3. The laminated gas sensor element as claimed in claim 1, wherein the porous protection layer has a thickness of 50 μm to 500 μm inclusive.

4. A gas sensor comprising a laminated gas sensor element as claimed in claim 1.

* * * * *